United States Patent [19]

Gallina

[11] Patent Number: 4,518,583

[45] Date of Patent: * May 21, 1985

[54] HEMORRHOID AND ANORECTAL DISEASE TREATMENT METHOD

[76] Inventor: Damian J. Gallina, 2856 W. 33rd St., Erie, Pa. 16506

[*] Notice: The portion of the term of this patent subsequent to Apr. 30, 2002 has been disclaimed.

[21] Appl. No.: 640,952

[22] Filed: Aug. 15, 1984

Related U.S. Application Data

[63] Continuation-in-part of Ser. No. 468,334, Feb. 22, 1983, abandoned.

[51] Int. Cl.$^3$ .............. A61K 31/17; A61K 31/79; A61K 31/675

[52] U.S. Cl. ..................... 424/80; 514/588; 514/714; 514/882

[58] Field of Search ............. 424/80, 338, 322

[56] References Cited

U.S. PATENT DOCUMENTS

| | | | |
|---|---|---|---|
| 1,071,186 | 8/1913 | Stern | 424/322 |
| 1,661,588 | 6/1923 | von Neergaard | 424/322 |
| 2,120,430 | 6/1923 | Rieche | 424/130 |
| 2,143,060 | 1/1939 | Dzialoschinsky et al. | 424/322 |
| 2,430,450 | 11/1947 | Brown | 424/130 |
| 2,436,673 | 2/1948 | Shelton | 424/130 |
| 2,542,898 | 2/1951 | Brown | 424/322 |
| 3,535,422 | 10/1970 | Cox et al. | 424/164 |
| 3,657,413 | 4/1972 | Rosenthal | 424/81 |
| 4,056,611 | 11/1977 | Young | 424/338 |
| 4,075,353 | 2/1978 | Mandy et al. | 424/338 |
| 4,163,800 | 8/1979 | Wickett et al. | 424/320 |
| 4,228,163 | 10/1980 | Bliss | 424/240 |
| 4,268,501 | 5/1981 | Konno et al. | 426/80 |
| 4,291,062 | 9/1981 | Leigh et al. | 424/322 |
| 4,302,441 | 11/1981 | Muhlemann et al. | 424/48 |
| 4,320,116 | 3/1982 | Bjorck | 424/129 |

*Primary Examiner*—Leonard Schenkman
*Attorney, Agent, or Firm*—Joseph P. Gastel

[57] ABSTRACT

A method of treating hemorrhoids and diseases of the anorectum by applying to hemorrhoidal or to inflamed or irritated anorectal tissues a treatment composition including by weight carbamide peroxide or benzoyl peroxide in an amount of between about 2% and 40%, an anesthetic in an amount of between about 0.5% and 25%, polyvinylpyrrolidone in an amount of between about 5% and 70% dissolved in glycerine in an amount of between about 10% and 90%, and appropriate surfactants, suspending agents, emollients, humectants and preservatives in an amount of between about 0.1% and 25%.

13 Claims, No Drawings

HEMORRHOID AND ANORECTAL DISEASE TREATMENT METHOD

CROSS REFERENCE TO RELATED APPLICATION

The present application is a continuation-in-part of application Ser. No. 468,334, filed Feb. 22, 1983, now abandoned.

BACKGROUND OF THE INVENTION

The present invention relates to an improved method for treating hemorrhoids and anorectal diseases by use of a preparation having cleansing, healing, antiseptic, re-epithelization, debriding, keratolytic properties.

By way of background, there are numerous preparations for treatment of hemorrhoids and anorectal diseases disclosed in the literature which include compounds for soothing and healing inflamed hemorrhoidal and anorectal tissues. U.S. Pat. No. 2,436,673 discloses the use of suppositories containing zinc peroxide for treatment of hemorrhoids. However, urea hydrogen peroxide, which is also known as carbamide peroxide and hydrogen peroxide carbamide, is not disclosed in the literature for treatment of hemorrhoids and other anorectal diseases including fissures, fistulas, etc.

In the past, urea hydrogen peroxide has been disclosed for use in oral and otic pharmaceutical preparations (U.S. Pat. Nos. 2,120,430, 3,657,413 and 4,302,441); for use as an antiseptic (U.S. Pat. No. 2,542,898); and for use as an antiseptic when used in combination with glycerol for promoting the healing of damaged tissues (U.S. Pat. No. 2,430,450). Urea, by itself has been mentioned for use in suppositories, but not as the chemical peroxide, urea hydrogen peroxide compound (U.S. Pat. Nos. 1,661,588 and 4,291,062). Also, benzoyl peroxide has been described for use as a skin treatment for such ailments as acne and seborrhea (U.S. Pat. Nos. 3,535,422, 4,056,611, 4,075,353, 4,163,800 and 4,228,163). U.S. Pat. No. 4,320,116 discloses a foodstuff and animal feed stuff containing an antibacterial system and teaches the use of carbamide peroxide for the foregoing purpose. However, none of the foregoing patents or other prior art known to applicant has ever used urea hydrogen peroxide or benzoyl peroxide in a formulation for treatment of hemorrhoids and other anorectal diseases.

SUMMARY OF THE INVENTION

It is accordingly one important object of the present invention to provide an improved method of treating hemorrhoids and other diseases of the anorectum including but not limited to fissures and fistulas, by using a preparation containing urea hydrogen peroxide or benzoyl peroxide for producing a healing, cleansing, debriding, keratolytic, antiseptic, and re-epithelization action on hemorrhoids and anorectal tissues.

It is a related object of the present invention to provide an improved method of treating hemorrhoids and anorectal diseases by the use of a composition having an urea hydrogen peroxide or benzoyl peroxide component and a vehicle having a sufficiently high molecular weight so that the vehicle is not adsorbed through the rectal membranes. Other objects and attendant advantages of the present invention will readily be perceived hereafter.

The present invention relates to a method of treating hemorrhoids and other anorectal diseases by applying to hemorrhoidal or anorectal tissues a treatment preparation comprising a peroxide selected from the group of urea hydrogen peroxide and benzoyl peroxide in a pharmaceutically effective amount for treatment of hemorrhoidal and anorectal tissues, and a vehicle containing said peroxide. In its more specific aspects, the vehicle comprises a compound having a sufficiently high molecular weight so as not to be adsorbed by the rectal mucosa. Also, in its more specific aspects, the preparation contains an anesthetic. The various aspects of the present invention will be more fully understood upon a reading of the following portions of the specification.

DESCRIPTION OF THE PREFERRED EMBODIMENTS

The improved hemorrhoidal and anorectal treatment composition used in the present method comprises urea hydrogen peroxide or benzoyl peroxide, an anesthetic and a vehicle, and is directed to the basic subject matter of copending application Ser. No. 475,342, which is an improvement over the subject matter of the present application. In addition, it may also contain such added items as aromatics and emulsifiers, such as menthol, Polysorbate 80, olive oil, lecithin, and an antifungal or preservative agent, as will appear more fully hereafter. The vehicle may be any one of numerous anhydrous innocuous watersoluble compounds which are commercially available.

The urea hydrogen peroxide, which is also known as carbamide peroxide and hydrogen peroxide carbamide, and which has a formula $CO(NH_2)_2 \cdot H_2O_2$, provides a cleansing, healing, and oxygenating action on hemorrhoid tissues and on anorectal tissues, such as fissures and fistulas. It decomposes to provide epidermal irrigation and desquamation (keratolysis), and produces bacteriostatic activity by way of damaging bacterial proteins. It also inhibits triglyceride (lipid and sebum) hydrolysis, thereby reducing levels of free fatty acids. This tends to decrease inflamation of surrounding tissues or lesions. The production of oxygen also demonstrates a mild astringent activity on injured tissue and, as noted above, hydrogen peroxide exerts a cleansing and debriding action through effervescent activity. The urea aids in solubilizing organic debris. Oxygen ($O_2$) stimulates re-epithelization of insured or denudated skin or tissue. The degradation byproducts of urea hydrogen peroxide are harmless and nontoxic if absorbed through the rectal mucosa. The urea hydrogen peroxide can be used in an amount of by weight of between about 2%–40%, and more preferably between about 5%–10%, and most preferably between about 7% and 10%. Benzoyl peroxide may be used in the foregoing amounts in place of carbamide peroxide as the oxygenating agent.

The improved composition also includes an anesthetic. This compound may be Lidocaine, which has the formula $C_{14}H_{22}N_2O$. It is known for use epidurally, intravenously for cardiac arrythmia, topically on mucous membranes and for peripheral nerveblock. Furthermore, it is an accepted safe and effective composition for external rectal use. Being an amide and nonester type of anesthetic, adverse and allegeric reactions to it are rare. Alternate types of anesthetics which can be used are known as dibucaine, diperidon, benzocaine, tetracaine, pramoxine, or others. The anesthetics may be present in an amount by weight from between about 0.25% to 25%, and more preferably between about 1% and 10%, and most preferably between about 1.5% to 10%.

The vehicle for the urea hydrogen peroxide or benzoyl peroxide and anesthetic is a viscous solution of polyvinylpyrrolidone dissolved in glycerine. Polyvinylpyrrolidone is also known as P.V.P. and Povidone and poly[1-(2-oxo-1-pyrrolidinyl)ethylene]. It is a white to creamy white odorless powder which is hygroscopic and is soluble in water, glycerol and alcohol. It has a molecular weight of 10,000 to 700,000. Its large molecular weight will prevent absorption through the rectal membranes. P.V.P. has been used as a plasma expander. It can be used in an amount by weight of between 5% and 70%, and more preferably between 20% and 50%, and most preferably between 30% and 50%. Glycerine ($C_3H_8O_3$) which is an accepted emollient, humectant, lubricant and vehicle is safe for internal use. It can be used in an amount by weight of between 5% and 90%, and more preferably between 7% and 70%, and most preferably between 10% and 50%.

The composition preferably also contains a suitable wetting, emulsifying, surfactant and suspending agent. One such agent is known as polysorbate 80 (sorbitan monooleate polyoxethylene) or (TWEEN 80). This or equivalent agents can be used in an amount of by weight of between about 1% and 30%, and more preferably between about 2% and 15%, and most preferably between about 5% and 10%.

The composition may also contain olive oil for use as an emulsifying and suspending agent, emollient and pharmaceutical vehicle. The olive oil may be present in an amount of by weight of between about 1% and 20%, and more preferably between about 2% and 15%, and most preferably between about 5% and 12%. Other acceptable oils may be used in lieu of olive oil.

An emulsifier which is safe for internal use is also used. Lecithin is preferred. It may be used by weight in an amount of between about 1% and 20%, and more preferably between about 1.5% and 15%, and most preferably between about 2% and 12%.

The composition may also contain an antibacterial or antifungal agent, such as methyl p-hydroxybenzoate, benzoic acid and/or acetone sodium bisulfite. Substances of this type are included for preventing bacterial or fungal growth. Suitable compounds are known under the trade names of Methylparaben and Propylparaben. The preservative agent may be present by weight in an amount of between about 0.1% and 2%, and more preferably between about 0.1% and 1%, and most preferably between about 0.25% and 0.75%.

Actual preparations have been formulated according to the following examples wherein the ingredients are listed in percentages by weight.

EXAMPLE 1

| | |
|---|---|
| Zinc Oxide | 5.00% |
| Urea hydrogen peroxide | 5.00% |
| Polyvinylpyrrolidone | 39.48% |
| Lidocaine | 3.80% |
| Glycerine | 30.24% |
| Polysorbate 80 | 4.76% |
| Olive oil | 7.14% |
| Methylparaben | .50% |
| Menthol | .50% |
| Resorcinol (1,3-benzenediol) | .190% |
| Oil of Eucalyptus | .5% |
| Lecithin | 2.89% |
| | 100.00% |

EXAMPLE 2

| | |
|---|---|
| Urea hydrogen peroxide | 5.00% |
| Polyvinylpyrrolidone | 44.48% |
| Lidocaine | 3.80% |
| Glycerine | 30.24% |
| Polysorbate 80 | 4.76% |
| Olive oil | 7.14% |
| Methylparaben | .50% |
| Menthol | .50% |
| Resorcinol (1,3-benzenediol) | .190% |
| Oil of Eucalyptus | .5% |
| Lecithin | 2.89% |
| | 100.00% |

EXAMPLE 3

| | |
|---|---|
| Urea hydrogen peroxide | 10.00% |
| Polyvinylpyrrolidone | 39.48% |
| Lidocaine | 3.80% |
| Glycerine | 30.24% |
| Polysorbate 80 | 4.76% |
| Olive oil | 7.14% |
| Methylparaben | .50% |
| Menthol | .50% |
| Resorcinol (1,3-benzenediol) | .190% |
| Oil of Eucalyptus | .5% |
| Lecithin | 2.89% |
| | 100.00% |

EXAMPLE 4

| | |
|---|---|
| Urea hydrogen peroxide | 10.00% |
| Polyvinylpyrrolidone | 40.17% |
| Lidocaine | 3.80% |
| Glycerine | 30.24% |
| Polysorbate 80 | 4.76% |
| Olive oil | 7.14% |
| Methylparaben | .50% |
| Menthol | .50% |
| Lecithin | 2.89% |
| | 100.00% |

EXAMPLE 5

| | |
|---|---|
| Benzoyl peroxide | 10.00% |
| Polyvinylpyrrolidone | 40.17% |
| Lidocaine | 3.80% |
| Glycerine | 30.24% |
| Polysorbate 80 | 4.76% |
| Olive oil | 7.14% |
| Methylparaben | .50% |
| Menthol | .50% |
| Lecithin | 2.89% |
| | 100.00% |

All of the above formulations were tested on subjects having from moderate to severe hemorrhoidal problems and relief from hemorrhoid or anorectal disease symptoms was obtained along with actual healing of the tissues.

As noted briefly above, the product can be formulated as a solid, gel, paste, cream, salve, ointment, liquid, and as a powder, depending on the ingredients and amounts used and depending on whether additional fats or solid greases are added.

While preferred embodiments of the present invention have been disclosed, it will be appreciated that it is not limited thereto, but may be otherwise embodied within the scope of the following claims.

What is claimed is:

1. A method of treating hemorrhoids and anorectal diseases by applying to hemorrhoids and anorectal tissues a composition comprising a peroxide selected from the group of urea hydrogen peroxide and benzoyl peroxide in a pharmaceutically effective amount for treatment of hemorrhoidal and anorectal tissues, and a vehicle.

2. A method for treating hemorrhoids and anorectal diseases as set forth in claim 1 wherein said peroxide is present by weight in an amount of between about 2% and 40%.

3. A method of treating hemorrhoids and anorectal diseases as set forth in claim 1 including an anesthetic.

4. A method of treating hemorrhoids and anorectal diseases as set forth in claim 3 wherein said peroxide is present by weight in an amount of between about 2% and 40% and wherein said anesthetic is present by weight in an amount of between about 0.5% and 25%.

5. A method of treating hemorrhoids and anorectal diseases as set forth in claim 1 wherein said vehicle includes polyvinylpyrrolidone.

6. A method of treating hemorrhoids and anorectal diseases as set forth in claim 5 wherein said polyvinylpyrrolidone is present by weight in an amount of between about 5% and 70%, and wherein said peroxide is present by weight in an amount of between about 2% and 40%.

7. A method of treating hemorrhoids and anorectal diseases as set forth in claim 6 wherein said polyvinylpyrrolidone is dissolved in glycerine.

8. A method of treating hemorrhoids and anorectal diseases as set forth in claim 7 wherein said glycerine is present by weight in an amount of between about 5% and 90%.

9. A method of treating hemorrhoids and anorectal diseases as set forth in claim 8 including an anesthetic present by weight in an amount of between about 0.25% and 25%.

10. A method of treating hemorrhoids and anorectal diseases as set forth in claim 1 wherein said vehicle comprises polyvinylpyrrolidone dissolved in glycerine.

11. A method of treating hemorrhoids and anorectal diseases as set forth in claim 10 wherein said peroxide is present by weight in an amount of between about 2% and 40%, wherein said polyvinylpyrrolidone is present by weight in an amount of between about 5% and 70%, and wherein said glycerine is present by weight in an amount of between about 5% and 90%.

12. A method of treating hemorrhoids and anorectal diseases as set forth in claim 9 including a wetting agent, a suspending agent, an emulsifying agent, and a preservative.

13. A method of treating hemorrhoids and anorectal diseases as set forth in claim 11 including a wetting agent, a suspending agent, an emulsifying agent, and a preservative.

* * * * *